(12) United States Patent
Ehlinger, Jr.

(10) Patent No.: US 7,062,320 B2
(45) Date of Patent: Jun. 13, 2006

(54) DEVICE FOR THE TREATMENT OF HICCUPS

(76) Inventor: Philip Charles Ehlinger, Jr., 2087 Turk Rd., Doylestown, PA (US) 18901

( * ) Notice: Subject to any disclaimer, the term of this patent is extended or adjusted under 35 U.S.C. 154(b) by 344 days.

(21) Appl. No.: 10/684,114

(22) Filed: Oct. 14, 2003

(65) Prior Publication Data
US 2005/0080458 A1   Apr. 14, 2005

(51) Int. Cl.
*A61N 1/04* (2006.01)
(52) U.S. Cl. .......................................................... 607/2
(58) Field of Classification Search .................. 607/1, 607/2, 3, 42, 47, 134, 139, 75, 40
See application file for complete search history.

(56) References Cited

U.S. PATENT DOCUMENTS

| 408,607 A | * | 8/1889 | Flint .......................... 607/134 |
| 4,210,141 A | * | 7/1980 | Brockman et al. ............ 604/78 |

* cited by examiner

Primary Examiner—George R. Evanisko
Assistant Examiner—Alyssa M. Alter
(74) Attorney, Agent, or Firm—Gregory J. Gore

(57) ABSTRACT

A device for the treatment of hiccups, and more specifically, to a method and apparatus for the treatment of hiccups involving galvanic stimulation of the Superficial Phrenetic and Vagus nerves using an electric current.

12 Claims, 2 Drawing Sheets

DEVICE FOR THE TREATMENT OF HICCUPS

BACKGROUND OF THE INVENTION

The present invention relates generally to a device for the treatment for hiccups, and more specifically, to a method and apparatus for the treatment of hiccups involving galvanic stimulation of the Superficial Phrenetic and Vagus nerves.

A Hiccup, also known as Hiccough, or Singultus, is an involuntary spasm of the diaphragm, resulting in an involuntary inhalation which is abruptly interrupted by the involuntary closing of the glottis, and resulting in the familiar and characteristic sound of a hiccup.

The exact anatomic and physiological mechanism responsible for causing hiccups remains unknown. Previous studies, such as "Hiccups," by P. Rosseau, M.D., Southern Medical Journal, Vol., 88, Pp. 175–181, 1995, attributed the hiccup reflexive arc to afferent and efferent nerve branches that are centrally connected between cervical segments 3 and 5. This branch encompasses the phrenic and vagus nerve fibers among others. It is the reflexive discharge of the phrenic nerve that results in the spasmodic contraction of the diaphragm, and that produces a hiccup.

The Merck Manual, Section 3, Chapter 21, "Functional UpperGastrointestinal Complaints," states that "Hiccups follow irritation of afferent or efferent nerves or of medullary centers that control the respiratory muscles, particularly the diaphragm. Afferent nerves may be stimulated by swallowing hot or irritating substances. High blood $CO_2$ irihibits hiccups; low $CO_2$ accentuates them. Hiccups are more common in men and often accompany diaphragmatic pleurisy, pneumonia, uremia, alcoholism, or abdominal surgery."

Hiccups lasting up to 48 hours are classified as "bouts". Hiccups lasting longer than 48 hours are called "persistent." Those lasting longer than a month are called "intractable."

Hiccups cures are ubiquitous and vary from the scientific to the absurd. Each "cure" achieves various levels of success based on individuals favorites, beliefs and anecdotal observations. Many simple cures involve increasing $Pa_{CO2}$ and inhibiting diaphragmatic activity by a series of deep breath-holdings or by rebreathing deeply into a paper bag. Simple activities that involve Vagal nerve stimulation are often recommended and can include drinking a glass of water rapidly, swallowing dry bread or crushed ice, inducing vomiting, or applying traction on the tongue or pressure on the eyeballs. Carotid sinus compression (massage) may be tried or strong digital pressure may be applied over the phrenic nerves behind the sternoclavicular joints.

Other maneuvers at the disposal of medical practitioners in treating patients with persistent or intractable Hiccups include esophageal dilation with a small bougie, galvanic stimulation of the phrenic nerve, and gastric lavage. Drugs can also be employed to control persistent hiccups including scopolamine, amphetamine, prochlorperazine, chlorpromazine, phenobarbital, and narcotics. Metoclopramide appears to help some patients. Nevertheless, successful treatment with drugs is often elusive. In troubling, refractory cases, the phrenic nerve may be blocked by small amounts of 0.5% procaine solution, although this extreme remedy risks respiratory depression and pneumothorax.

U.S. Pat. No. 6,152,953 (2000) "Device for the treatment of Hiccups" employed a physiological cold block to the Phrenetic and Vagus nerves. The stated physiological conditions and implications with this prior Patent are similar to the instant case. However the means, methods and apparatus are entirely unique to this application. The present Invention is superior to this prior art because it does not require a cold source or the access to refrigeration equipment and electricity. The present invention also is faster acting in that it does not require the user to wear an appliance around their neck for an extended period of time. Rather the present invention can treat hiccups during the act of consumption of a potable liquid from the device and relief can be obtained quickly.

The aforementioned plurality of suggested treatments for the Hiccups indicates that no single, effective and reliable treatment exists. The present invention fulfills the need for a safe, simple and effective treatment and provides unique advantages over prior art.

BRIEF SUMMARY OF THE INVENTION

The object of the present invention is to galvanically stimulate the superficially coursing vagus and phrenic nerves in order to reliably interrupt the Hiccup Reflexive Arc. To achieve this object, the present invention provides a method and apparatus for the treatment of hiccups involving galvanic stimulation of the superficially coursing phrenic and vagus nerves utilizing an cup-like appliance designed for the containment and human consumption of a conductive potable liquid such as tap water. The present invention includes a first electrode of an electrically conductive material integrated into the body of the vessel, and a second electrode of electrically conductive material also integrated into the body of the vessel. The electrically conductive materials constituting the first and second electrodes have different electrochemical potentials. When the vessel is filled with an electrically conductive potable liquid, such as tap water, the electrodes are immersed in said liquid. Thus, an electric potential is developed by and between the electrodes. The second electrode is also configured as to make contact with the temple and cheek region of the face when drinking liquids from the cup-like vessel. During typical human oral consumption of the liquid from the lip of the cup-like vessel of the present invention, an electrical circuit is created and the electro-chemically produced potential energy, or Ions, are conducted through the electrodes and the electro-conductive liquid to the user's lips, mouth and throat as well as the temple region of the face, thus stimulating the superficially coursing vagus and phrenic nerves and reliably interrupting the Hiccup Reflexive Arc.

According to the unique features of the present invention, the preferred embodiment is a cup-like vessel that is constructed of a carbon based metal with a specific electrochemical potential which serves as the first electrode. The second electrode is a copper alloy material which has a dissimilar electrochemical property than the carbon based metal of the vessel body. The first electrode is electrically insulated from the second electrode except when the vessel is filled with an electrically conductive liquid such as tap water. During use, significant surface area of both electrodes are in contact with the liquid. One electrode is in contact with the lips and mouth, and the second electrode is in contact with the temple or cheek region of the face. Thus a flow of Ions is created by the electrochemical potentials of the dissimilar metal electrodes and is conducted through the body tissues sufficiently to interrupt the Hiccup Reflexive Arc.

In another embodiment of the invention, the vessel is constructed of any suitable non-conductive materials such as plastic, and the electrodes are formed of electrically conductive materials in the shape of segments of the vessel, which are integrated into the insulative plastic material. In yet another embodiment, the electrodes are applied to an existing drinking vessel constructed of any material. The detailed description of the drawings will further explain the objects and advantages of the present invention

BRIEF DESCRIPTION OF THE DRAWINGS

FIG. 3 is a top plan view of the device in FIG. 1.

DETAILED DESCRIPTION OF THE INVENTION

Figure 1:
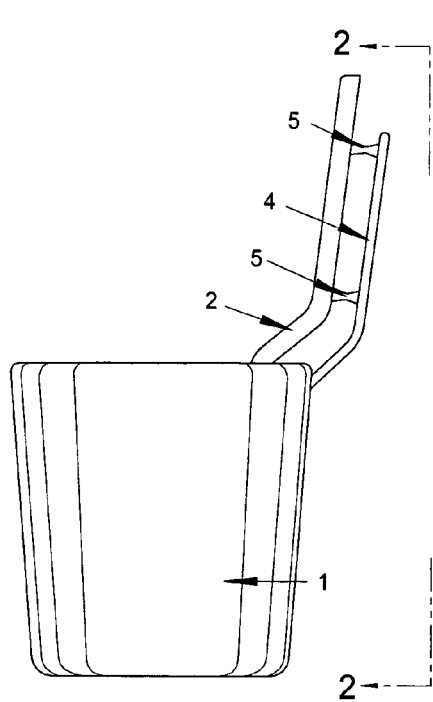
FIG. 1 is a side view of the device for the treatment of hiccups embodying the preferred practice of the present invention.
Figure 2:
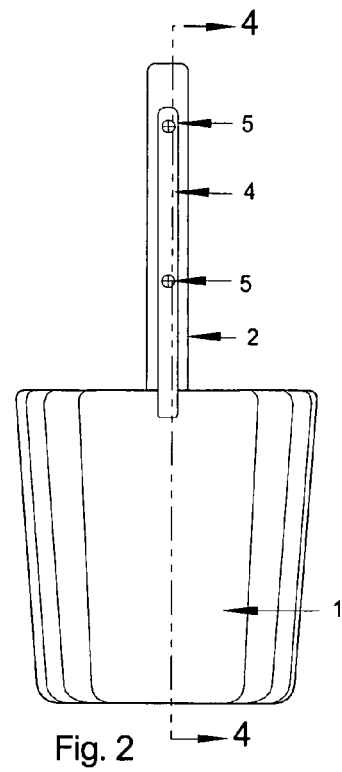
FIG. 2 is a side elevation view of the device of FIG. 1 as seen substantially from a plane indicated by a line 2—2 in FIG. 1.
Figure 3:
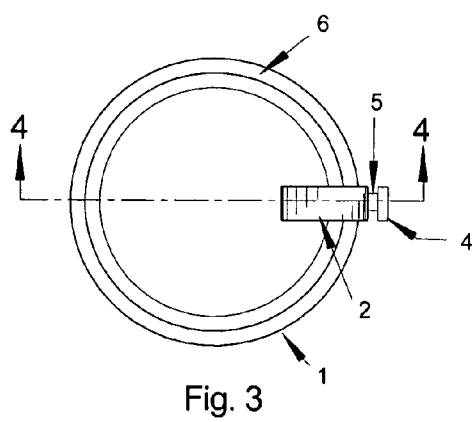
FIG. 3 is a top plan view of the appliance in FIG. 1.
Figure 4:
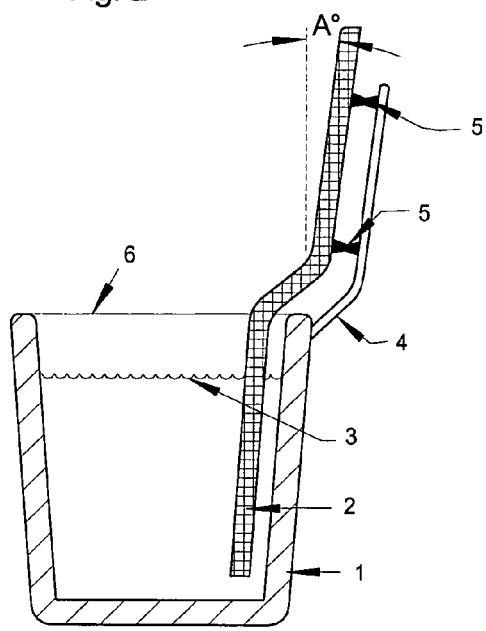
FIG. 4 is a sectional view as seen from a plane indicated by a line 4-4 in FIG. 2 & FIG. 3
Figure 5:
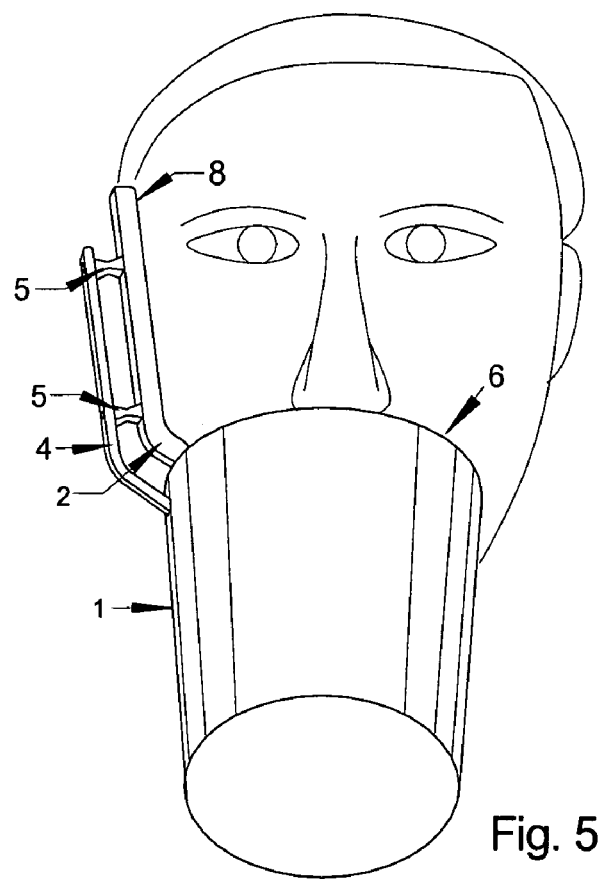
FIG. 5 is a schematic front view illustrating the device of FIG. 1 during use.
Figure 6:
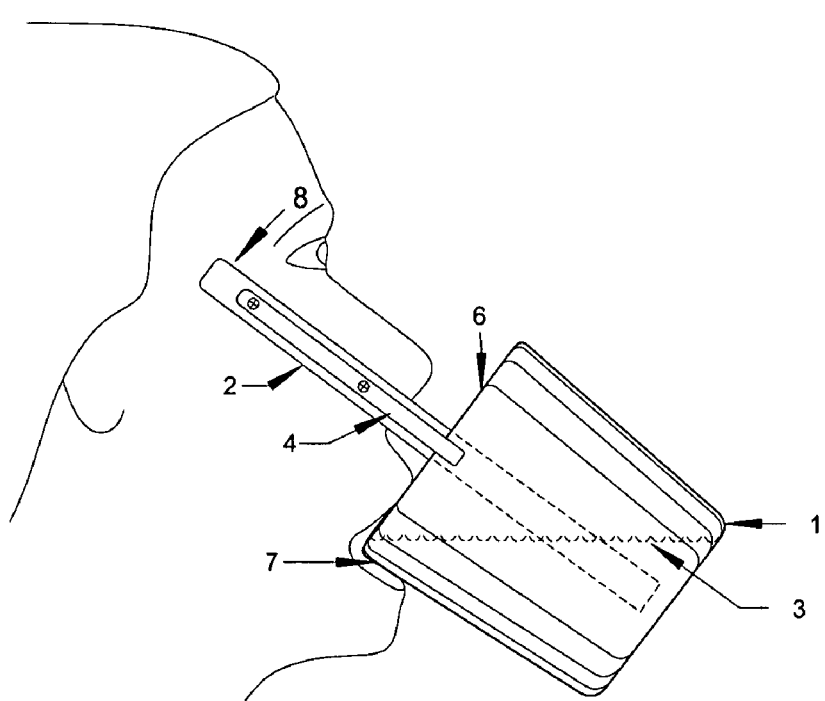
FIG. 6 is a schematic side view illustrating the device of FIG. 1 during use.

Referring first to FIG. 1, the Device for the Treatment of Hiccups of the present invention includes a cup like vessel designed for the containment and consumption of potable liquids 1, which also serves as the first electrode, and a second electrode 2, which is supported by a bracket 4. The second electrode 2 is electrically insulated from the bracket 4 and the first electrode 1 by a non-conductive insulator 5. As shown in FIGS. 2 & 3. the support bracket 4 is of similar dimension to second electrode 2 with connecting insulators 5 creating a gap between them. The second electrode 2 is configured as to make contact with the user's skin in the region of the face and temple 8 as can be seen in FIGS. 5 & 6. The configuration of the second electrode 2 can be best seen in the cross-sectional view of FIG. 4, which illustrates how the second electrode 2 is immersed in a conductive liquid 3 during the act of drinking from the lip 2 of the user and then extends a distance above the rim 6 of the vessel 1 and is configured at an optimal angle A to make contact with the skin in the temple and cheek region 8 of the head.

REFERENCES CITED

| U.S. Patent Documents | | | |
|---|---|---|---|
| 5861022 | January 1999 | Hipskind | 607/109. |

OTHER REFERENCES

Lewis, James H., M.D., "Hiccups: Causes and Cures," Journal of Clinical Gastroenterology, vol. 7(6), December 1985, pp. 539–552.

Noble, E. Clark, *"Hiccup,"* The Canadian Medical Association Journal, July 1934, pp. 38–41.

Travell, Janet G., M.D., "A Trigger Point for *Hiccup*," The Journal of the American Osteopathic Association, vol. 77, December 1977, pp. 308–312.

Rousseau, Paul, M.D., "Hiccups," Southern Medical Journal, vol. 88, No. 2, February 1995, pp. 175–181.

Launois, S., et al., *"Hiccup* in Adults: An Overview," European Respiratory Journal, vol. 6, No. 4, April 1993, pp. 563–575.

Hulbert, N. G., M.D., "Hiccoughing," The Practitioner, vol. 167., September 1951, pp. 286–289.

What is claimed is:

1. A device for curing hiccups, comprising:
   a metallic cup-like vessel being a first electrode for producing electricity adapted to be applied to the lip of the user; and
   a second electrode electrically insulated from said first electrode being affixed to said vessel and extending from a point substantially within said vessel to a point substantially above a rim of the vessel.

2. The device of claim 1 further including an elongate bracket affixed to a wall of said vessel and to said second electrode to support said second electrode in spaced relation thereto, said bracket extending above the rim of the vessel.

3. The device of claim 7 further including at least one insulator located between said bracket and said second electrode to provide a non-conductive attachment of said electrode to said bracket whereby a conductive liquid within said vessel causes a galvanic response between said first and second electrodes to produce an electrical potential therebetween.

4. The device of claim 3 wherein said vessel is composed of a carbon-based metal.

5. The device of claim 3 wherein said second electrode is composed of a material that is of a different electrochemical potential than the metal of said vessel.

6. The device of claim 5 wherein said second electrode is composed of a carbon alloy.

7. The device of claim 1 wherein said metallic electrode contains a distal region thereof located above the rim and adapted to contact the facial skin in the temple region of the user when drinking from the vessel.

8. The device of claim 7 wherein the vessel and second electrode are adapted to apply an electrical potential between the user's facial temple region and parts of the user's body in contact with the electrically conductive liquid within said vessel.

9. The device of claim 8 wherein said conductive liquid is water.

10. A method of curing hiccups, comprising:
    applying a first electrical current of one potential to the lower lip of the patient; and
    applying a second electrical current of a different potential from said one potential to the facial skin of the patient.

11. The method of claim 10 further including the step of drinking an electrically conductive fluid from a vessel which includes the electrodes for applying said first and second electrical currents to the patient.

12. The method of claim 11 wherein the body of the vessel provides a first electrode for applying the first electrical current and a second electrode which applies the second electrical current is non-conductively affixed to a wall of the vessel and is immersed at one end in the electrically conductive fluid.

* * * * *